(12) United States Patent
Greenfield

(10) Patent No.: US 7,077,827 B2
(45) Date of Patent: Jul. 18, 2006

(54) SYRINGE FOR SEQUENTIAL DELIVERY OF DIFFERENT FLUIDS

(76) Inventor: Christian John Greenfield, 827 Morado Pl., Oxnard, CA (US) 93030

( * ) Notice: Subject to any disclaimer, the term of this patent is extended or adjusted under 35 U.S.C. 154(b) by 165 days.

(21) Appl. No.: 10/788,713

(22) Filed: Feb. 27, 2004

(65) Prior Publication Data

US 2004/0171984 A1 Sep. 2, 2004

Related U.S. Application Data

(63) Continuation-in-part of application No. 10/231,827, filed on Aug. 30, 2002, now abandoned.

(51) Int. Cl.
*A61M 5/00* (2006.01)

(52) U.S. Cl. .......................................... 604/191; 604/82
(58) Field of Classification Search ............. 604/88–92, 604/82, 86, 87, 191, 201, 203, 244, 416, 604/181, 187, 199, 200, 204, 212, 214, 232, 604/236, 190, 110, 220, 222
See application file for complete search history.

(56) References Cited

U.S. PATENT DOCUMENTS

| | | | | |
|---|---|---|---|---|
| 3,489,147 A | * | 1/1970 | Shaw | 604/88 |
| 3,636,950 A | * | 1/1972 | Gomez et al. | 604/416 |
| 3,659,749 A | | 5/1972 | Schwartz | 222/145 |
| 3,923,058 A | | 12/1975 | Weingarten | 128/218 |
| 4,055,177 A | * | 10/1977 | Cohen | 604/88 |
| 4,113,097 A | | 9/1978 | Finn | 206/528 |
| 4,215,701 A | | 8/1980 | Raitto | 128/763 |
| 4,439,184 A | * | 3/1984 | Wheeler | 604/90 |
| 4,702,737 A | | 10/1987 | Pizzino | 604/191 |
| 5,102,388 A | * | 4/1992 | Richmond | 604/88 |
| 5,476,449 A | | 12/1995 | Richmond | 604/87 |
| 5,577,513 A | | 11/1996 | Van Vlasselaer | 128/765 |
| 5,743,879 A | | 4/1998 | Kriesel | 604/132 |
| 6,544,233 B1 | * | 4/2003 | Fukui et al. | 604/191 |

* cited by examiner

*Primary Examiner*—Manuel Mendez
(74) *Attorney, Agent, or Firm*—Michael A. O'Neil

(57) ABSTRACT

A syringe for sequentially administering different fluids includes a floating piston which separates the syringe into a first portion for receiving a first fluid to be administered and a second portion for receiving a second fluid to be administered. The floating piston includes a fluid tight seal which initially separates the first and second portions of the syringe and apparatus for connecting the second portion of the syringe to the syringe needle after the first fluid has been discharged from the syringe.

34 Claims, 4 Drawing Sheets

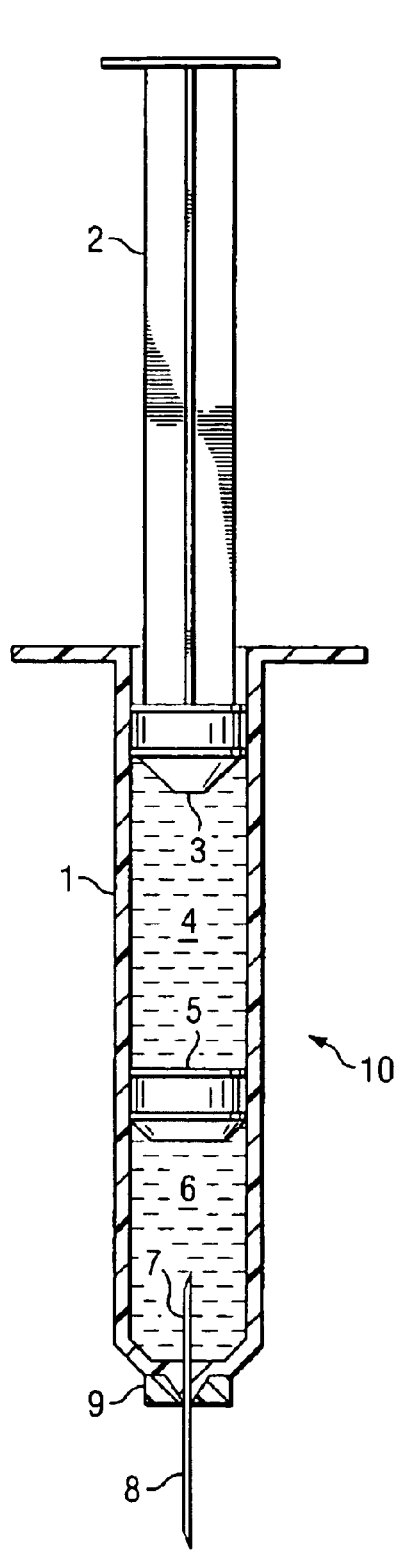
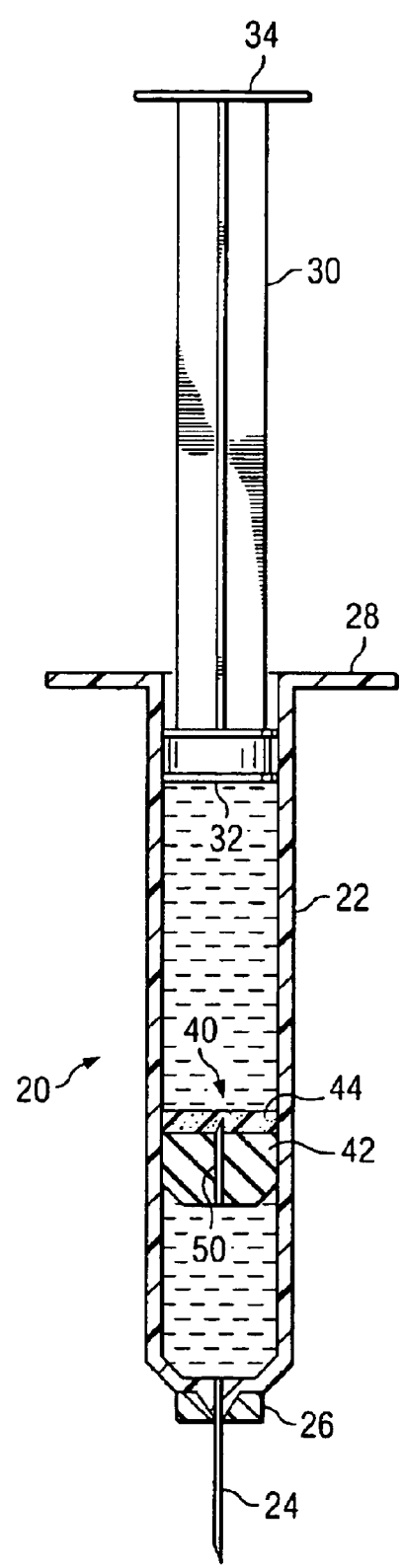
FIG. 1
(PRIOR ART)
FIG. 2

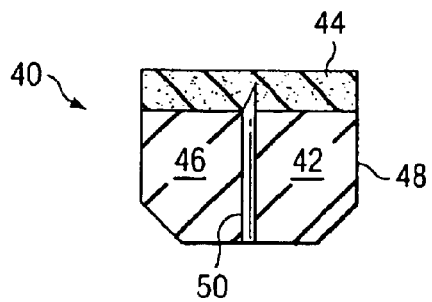
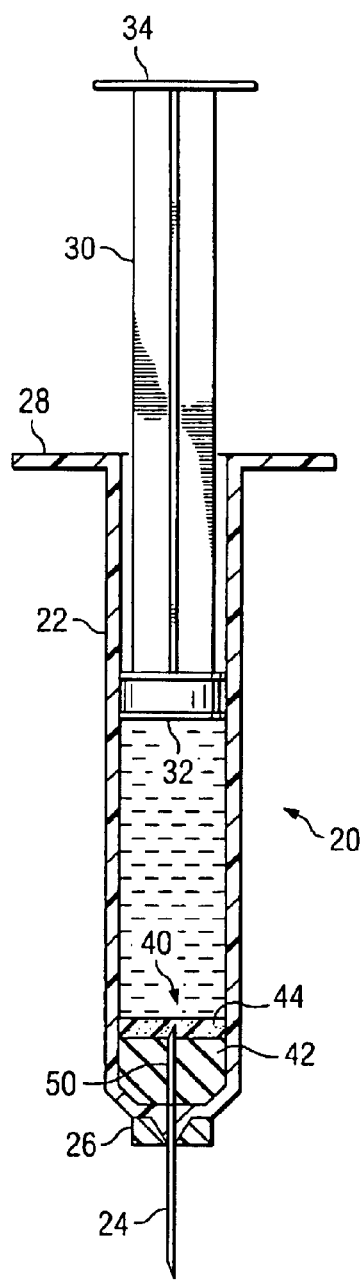
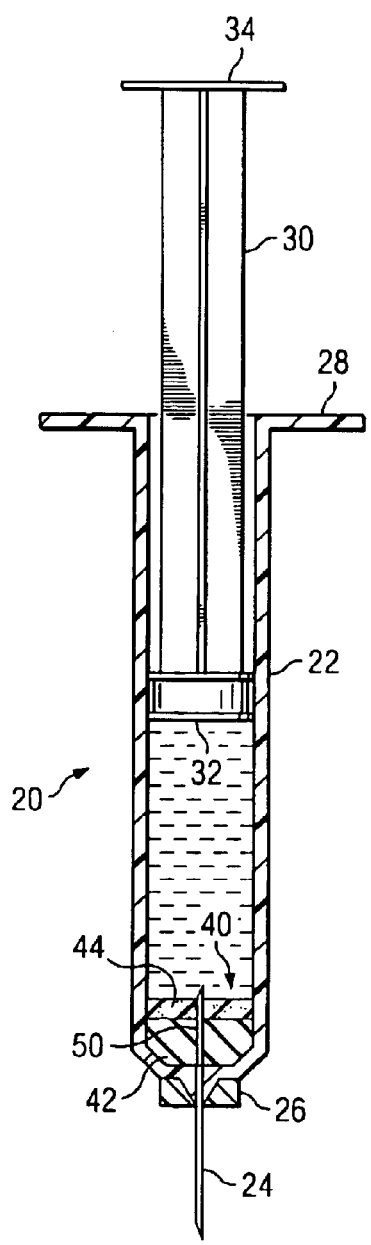
FIG. 3
FIG. 4
FIG. 5

SYRINGE FOR SEQUENTIAL DELIVERY OF DIFFERENT FLUIDS

CROSS-REFERENCE TO RELATED APPLICATIONS

This application is a continuation-in-part application of application Ser. No. 10/231,827 filed Aug. 30, 2002 abandoned.

TECHNICAL FIELD

This invention relates generally to the sequential administration of different fluids, for example, the administration of a medication followed immediately by the administration of a normal saline solution, and more particularly to an improved syringe design which assures complete delivery of the first fluid followed immediately by complete delivery of the second fluid.

BACKGROUND AND SUMMARY OF THE INVENTION

Various medical procedures require the sequential administration of different fluids. For example, administration of the cardiac drug known as Adenosine must be followed immediately by the administration of a normal saline solution in order to get the drug into circulation rapidly. Heretofore the sequential administration of different fluids has been accomplished utilizing two syringes, one loaded with the first fluid to be administered and the other loaded with the second fluid to be administered. The two needle system is not only awkward but also increases the risk that medical personnel will suffer inadvertent needlesticks.

A previous attempt to solve the foregoing problem is shown and described in published U.S. patent application Ser. No. 2002-0035351-A1. Referring to FIG. 1 of the present application, the device disclosed in the published application comprises a single barrel double chamber syringe 10 having a barrel 1 and a plunger 2 which is utilized in the conventional manner to force fluids contained within the barrel 1 outwardly through a hollow needle 8. This is accomplished by means of a push stopper 3 secured to the plunger 2 and made of a pliable material to maintain a fluid tight seal around its outer periphery. A hollow floating plunger 5 situated within the barrel 1 is likewise comprised of a pliable material to maintain a fluid tight seal around its outer periphery. The floating plunger 5 divides the barrel 1 into a first compartment 4 and a second compartment 6.

The hollow needle 8 is secured in a hub 9 situated at the opposite end of the barrel 1 from the plunger 2. The hollow needle 8 comprises a first component extending outwardly from the barrel 1 and the hub 9 and a piercing component extending from the hub 9 into the second compartment 6 of the barrel 1. The hollow needle 8 is provided with a porthole 7 to assure full delivery of fluid contained within the second compartment 6.

In the operation of the syringe 10 a first fluid is loaded into the second compartment 6 and a second fluid is loaded into the first compartment 4. As the push stopper 3 is forced downwardly (FIG. 1) into the barrel 1 under the action of the plunger 2, the fluid within the first compartment 4 and the floating plunger 5 function to force the first fluid outwardly from the second compartment 6 through the hollow needle 8. As the floating plunger 5 moves downwardly it eventually engages the piercing component of the hollow needle 8 which begins to penetrate the floating compartment 5. Meanwhile, the remainder of the first fluid is forced out of the second compartment 6 through the porthole 7 and the hollow needle 8.

Continued downward movement of the push stopper 3 under the action of a plunger 2 causes the piercing component of the hollow needle 8 to fully pierce the floating plunger 5 thereby allowing the second fluid to flow outwardly from the first compartment 4 through the hollow needle 8. Movement of the push stopper 3 toward the hollow needle 8 under the action of the plunger 2 continues until all of the second fluid has been discharged from the syringe 10 through the hollow needle 8.

While eliminating the problems inherent in sequentially administering two different fluids utilizing two syringes, the device shown and described in published application US-2002-0035351-A1 involves different problems. First, the hollow needle through which the different fluids are sequentially administered must be provided with a porthole. As will be appreciated by those skilled in the art, forming a porthole in a hollow needle of the type utilized in medical syringes involves difficult and expensive manufacturing steps. Second, the axial dimensions of the hollow needle utilized in the device disclosed in the published application must be very accurately controlled. Thus, if the piercing component of the needle is too short the floating plunger will not be properly penetrated thereby preventing proper administration of the second fluid. Conversely, if the piercing component of the hollow needle is too long complete delivery of the first fluid cannot be assured.

The present invention comprises an improved syringe design which overcomes the foregoing and other problems that have long since characterized the prior art. In accordance with a first embodiment of the invention an otherwise conventional syringe is provided with a floating piston comprising upper and lower portions. The lower portion may comprise a spongy material encased in a flexible shell and having a piercing needle mounted therein. Alternatively, the lower portion may comprise a flexible shell filled with a suitable gas such as air. The upper portion comprises a seal formed from a non-coring elastomeric material.

In the practice of the first embodiment of the invention a first fluid to be administered is loaded into the barrel of the syringe below the floating piston. A second fluid to be delivered is loaded into the barrel of the syringe above the floating piston. As the plunger of the syringe is moved into the barrel, the first fluid is forced outwardly through the needle of the syringe under the action of the second fluid and the floating piston. The floating piston eventually engages the discharge end of the barrel thereby forcing the entirety of the first fluid outwardly through the needle. Continued movement of the plunger of the syringe causes the penetrating needle of the floating piston to penetrate the seal comprising the upper portion of the floating piston. At this point the second fluid is connected in fluid communication with the syringe needle through the penetrating needle of the floating piston. Further inward movement of the plunger of the syringe forces all of the second fluid outwardly through the penetrating needle of the floating piston and the syringe needle.

In accordance with a second embodiment of the invention an otherwise conventional syringe is divided into upper and lower chambers by a floating piston. The floating piston comprises a resilient, spongy material and has an aperture extending therethrough from top to bottom. The aperture may be axially disposed and circular in cross-section, however, neither the location nor the shape of the aperture is critical to the practice of the invention. A substantially rigid valve extends through the aperture of the floating piston. The upper end of the valve comprises an imperforate sealing disk. The lower end of the valve comprises an open construction to allow the passage of fluid therethrough.

The length of the valve is slightly less than the thickness of the floating piston such that the piston is normally slightly compressed thereby maintaining the sealing disk in sealing engagement with the upper end of the passageway. As the plunger of the syringe is moved axially through the barrel thereof toward the needle of the syringe, the fluid in the portion of the barrel extending above the floating piston forces the floating piston toward the needle of the syringe thereby forcing the fluid in the lower portion of the barrel of the syringe outwardly through the needle. When the floating piston bottoms out at the needle end of the syringe, further movement of the plunger compresses the spongy material comprising the floating piston thereby disengaging the sealing disk from the upper end of the passageway through the floating piston. This allows the fluid that was originally in the end of the barrel of the syringe remote from the needle thereof to pass through the aperture in the floating piston and outwardly through the needle of the syringe.

BRIEF DESCRIPTION OF THE DRAWINGS

A more complete understanding of the invention may be had by reference to the following Detailed Description when taken in conjunction with the accompanying Drawings, wherein:

FIG. 1 is a longitudinal sectional view of a prior art single barrel double chamber syringe;

FIG. 2 is a longitudinal sectional view of a first embodiment of the syringe of the present invention showing the syringe in a first stage of its operation;

FIG. 3 is an enlargement of a portion of FIG. 2;

FIG. 4 is a view similar to FIG. 2 showing the syringe at a later stage in its operation;

FIG. 5 is a view similar to FIG. 2 showing a syringe of the present invention at a still later stage in its operation;

DETAILED DESCRIPTION

Figure 6:
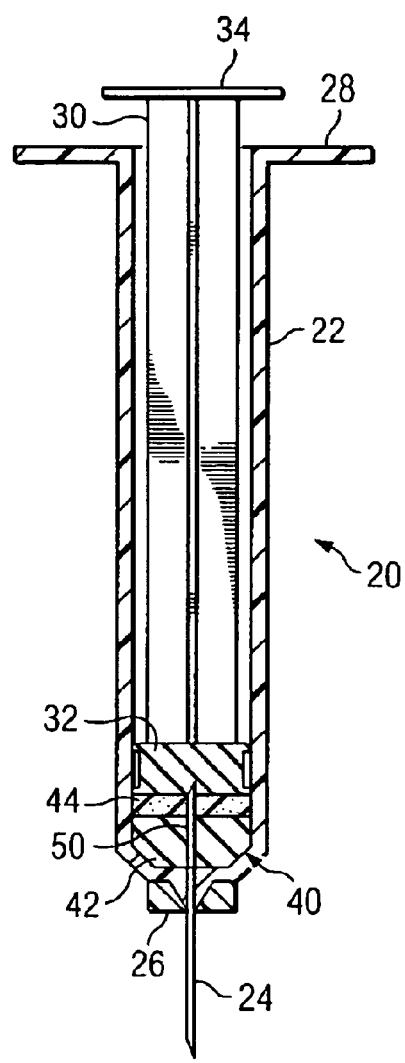
FIG. 6 is an illustration similar to FIG. 2 showing a syringe of the present invention at the completion of its operation.

Referring now to the Drawings, and particularly to FIG. 2 thereof, there is shown a syringe 20 comprising a first embodiment of the present invention. In many respects the syringe 20 is conventional in construction and operation. Thus, the syringe 20 includes a barrel 22 which receives fluid to be administered. A hollow needle 24 is secured to one end of the barrel 22 by a hub 26 and is coupled in fluid communication with the interior of the barrel 22. The end of the barrel 22 remote from the needle 24 may be provided with a radially extending flange 28 which is typically engaged by the fingers of an individual operating the syringe 20.

The syringe 20 further includes a plunger 30 adapted for axial movement within the barrel 22. The plunger 30 extends to a piston 32 which forms a fluid tight seal with the interior surface of the barrel 22. The end of the plunger 30 remote from the piston 32 may be provided with a plate 34 which is typically engaged by the thumb of an individual operating the syringe 20.

Referring to FIGS. 2 and 3, the syringe 20 differs from conventional syringes in that it is provided with a floating piston 40. The floating piston 40 includes a lower portion 42 and an upper portion 44.

Referring particularly to FIG. 3, the lower portion 42 of the floating piston 40 comprises a body 46 formed from a resilient material which may be spongy in nature. The body 46 is surrounded by a flexible layer 48 formed from a material approved for medical applications, for example, silicone. Alternatively, the lower portion 42 may comprise a flexible shell filled with a suitable gas such as air. The lower portion 42 of the floating piston 40 further comprises a piercing needle 50. The piercing needle 50 is mounted and supported by the body 46 of the lower portion 42 of the floating piston 40.

The piercing needle 50 is hollow throughout its length and is preferably either equal to or greater in diameter than the needle 24 of the syringe 20. The piercing needle 50 may be provided with an enlarged portion at the end thereof facing the needle 24 of the syringe 20 in order to assure fluid communication between the piercing needle 50 and the hollow needle 24.

The upper portion 44 of the floating piston 40 comprises a non-coring elastomeric material. In use, the upper portion 44 forms a fluid tight seal with the interior surface of the barrel 22 of the syringe 20. As will be appreciated by those skilled in the art, the function of the lower portion 42 of the floating piston 40 is to divide barrel 22 of the syringe 20 into upper and lower chambers and to initially maintain a fluid-tight barrier therebetween.

Operation of the syringe 20 is illustrated in FIGS. 2, 4, 5, and 6. Referring first to FIG. 2, a first fluid to be administered is loaded into the portion of the barrel 22 of the syringe 20 situated below the floating piston 40. A second fluid to be administered immediately following completion of the delivery of the first fluid is loaded into the portion of the barrel 22 of the syringe 20 situated above the floating piston 40. The floating piston 40, and particularly the upper portion 42 thereof, comprises a fluid tight seal which maintains separation between the two fluids.

Referring next to FIG. 4, administration of the first fluid is accomplished by moving the plunger 30 inwardly, that is, from the position illustrated in FIG. 2 toward the position illustrated in FIG. 4. As the plunger 30 is moved inwardly, the floating piston 40 and the second fluid positioned within the barrel 22 of the syringe 20 betweeen the floating piston 40 and the plunger 30 function to force the first fluid out of the barrel 22 through the hollow needle 24. FIG. 4 illustrates the floating piston 40 bottomed out in,the barrel 22 of the syringe 20 with all of the first fluid having been delivered through the hollow needle 24.

Referring next to FIG. 5, further inward movement of the piston 32 compresses the resilient material 46 and/or the gas comprising the lower portion 42 of the floating piston 40 thereby causing the piercing needle 50 to penetrate the upper portion 44 of the floating piston 40. In this manner the second fluid to be administered, which is situated between the floating piston 40 and the plunger 30, is connected in fluid communication with the hollow needle 24 through the hollow interior of the piercing needle 50. Further inward movement of the plunger 30 forces the second fluid to be administered out of the barrel 22 of the syringe 20 through the piercing needle 50 and the hollow needle 24. This action continues until the piston 32 of the plunger 30 bottoms out as illustrated in FIG. 6. At this point the syringe 20 is typically disposed of in accordance with approved syringe disposal techniques.

Referring to FIGS. 7 through 10, inclusive, there is shown a syringe 60 comprising a second embodiment of the present invention. In many respects the syringe 60 is conventional in construction and operation. Thus, the syringe 60 includes a barrel 62 which receives fluid to be administered. A hollow needle 64 is secured to one end of the barrel 62 by a hub 66 and is coupled in fluid communication with the interior of the barrel 62. The end of the barrel 62 remote from the needle 64 may be provided with a radially extending flange 68 which is typically engaged by the fingers of an individual operating the syringe 60.

The syringe 60 further includes a plunger 70 adapted for axial movement within the barrel 62. The plunger 70 extends to a piston 72 which forms a fluid tight seal with the interior surface of the barrel 62. The end of the plunger 70 remote from the piston 72 may be provided with a plate 74 which is typically engaged by the thumb of an individual operating the syringe 60.

The syringe 60 differs from conventional syringes in that it is provided with a floating piston 80. The floating piston 80 includes a body 82 formed from a spongy, resilient material. As will be apparent to those skilled in the art, it is necessary that the body 82 is formed from a material having sufficient resiliency to form a fluid tight seal with the interior wall of the barrel 62. The floating piston 80 further includes a valve 84 which is formed from a substantially rigid material. Both the body 82 and the upper portion 44 are formed from materials which are impervious to attack by the fluids which are administered by the syringe 60.

Figure 9:
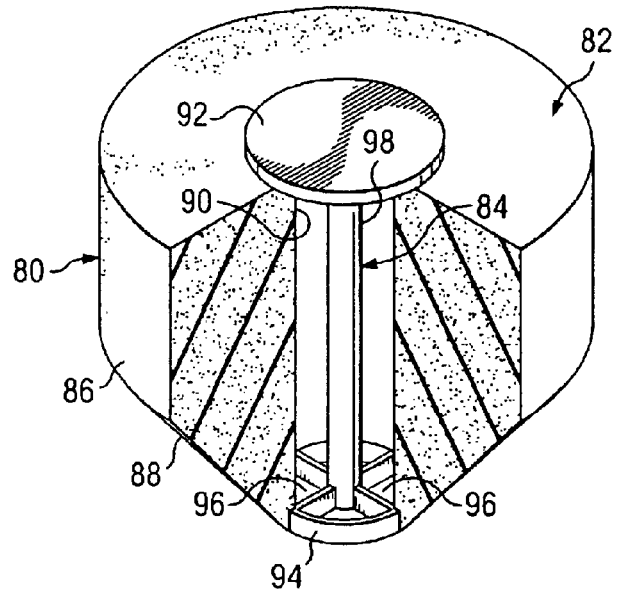
FIG. 9 is a partial perspective view of the floating piston of the syringe of FIG. 7.
Figure 10:
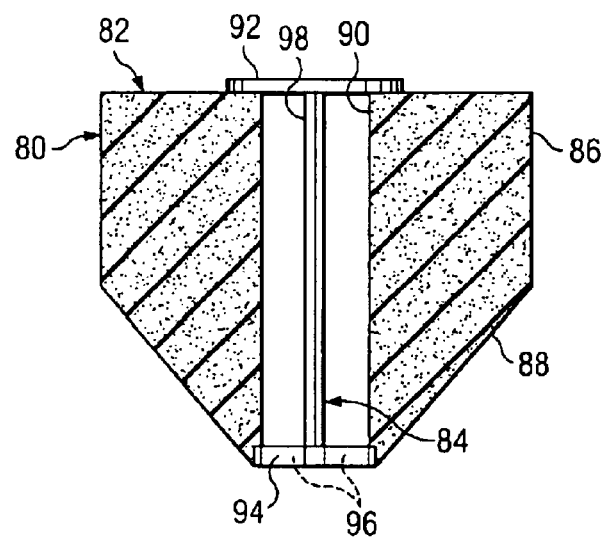
FIG. 10 is a sectional view further illustrating the floating piston of the syringe of FIG. 7.

Referring to FIGS. 9 and 10, the body 82 of the floating piston 80 includes an upper portion 86 comprising a right circular cylinder and a lower portion 88 comprising a truncated cone. A passageway 90 extends entirely through the body 82 from the top to the bottom thereof. The passageway 90 may extend along the axis of the body 82 and may be circular in cross section, wherever, other locations and other cross sectional configurations of the passageway 90 may be utilized in the practice of the invention depending upon the requirements of particular applications thereof.

The valve 84 includes an imperforate top plate 92 which normally seals the upper end of the passageway 90 formed in the body 82. The lower end of the valve 84 comprises a perforated plate 94 comprising a plurality of apertures 96 which facilitate fluid flow through the lower end of the passageway 90. A rod 98 connects the imperforate top plate 92 to the perforated lower plate 94.

Figure 7:
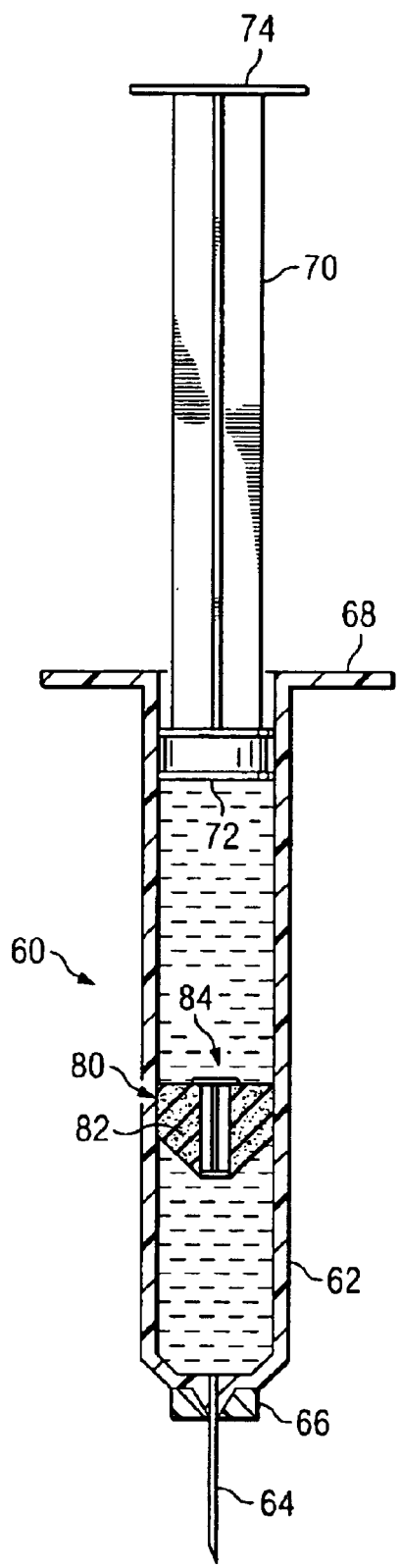
FIG. 7 is a longitudinal sectional view of a second embodiment of the syringe of the present invention showing the syringe in a first stage of its operation.
Figure 8:
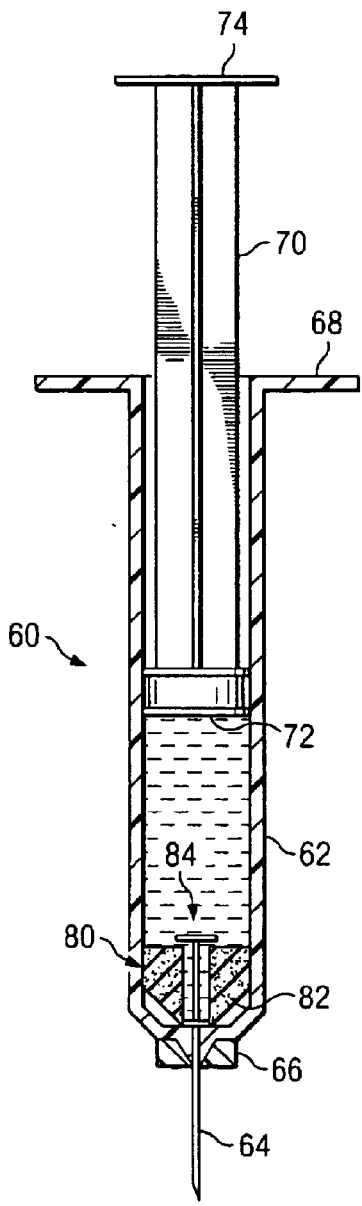
FIG. 8 is a view similar to FIG. 7 showing the syringe at a later stage in its operation.

Operation of the syringe 60 is illustrated in FIGS. 7 and 8. Referring first to FIG. 7, a first fluid to be administered is loaded into the portion of the barrel 62 of the syringe 60 situated below the floating piston 80. A second fluid to be administered immediately following completion of the delivery of the first fluid is loaded into the portion of the barrel 62 of the syringe 60 situated above the floating piston 80. The floating piston 80, and particularly the body 82 thereof forms a fluid tight seal which maintains a separation between the two fluids.

The administration of the first fluid is accomplished by moving the plunger 70 inwardly, that is, from the position illustrated in FIG. 7 toward the position illustrated in FIG. 8. As the plunger 70 is moved inwardly, the floating piston 80 and the second fluid positioned within the barrel 62 of the syringe 60 between the floating piston 80 and the plunger 70 function to force the first fluid out of the barrel 62 through the hollow needle 64. FIG. 6 illustrates the floating piston 80 bottomed out in the barrel 62 of the syringe 60 with all of the first fluid having been delivered through the hollow needle 64.

Further inward movement of the piston 72 compresses the material comprising the body 82 of the floating piston 80. Due to the relative rigidity of the valve 84 as compared with the relative compressibility of the material comprising the body 82, compression of the body 82 of the floating piston 80 under the action of the plunger 70 causes separation between the top of the passageway 90 formed through the body 82 of the floating piston 80 and the imperforate top plate 92 of the valve 84. Such separation opens the passageway 90 through the body 82 thereby allowing the second fluid to flow through the body 82 of the floating piston 80 and through the needle 64 for administration to the patient. Inward movement of the plunger 70 continues until all of the fluid that was originally contained in the portion of the barrel 62 located between the plunger 70 and the floating piston 80 is dispensed.

It will therefore be understood that the present invention comprises a syringe for sequentially administering different fluids which overcomes the problems that have characterized the prior art. In particular, manufacture of the syringe of the present invention involves the addition of a unique floating piston to an otherwise conventional syringe. Manufacture of the component parts of the syringe of the present invention does not involve complicated and expensive manufacturing techniques, nor does it involve precise control over the dimensions of the component parts of the device.

Although preferred embodiments of the invention have been illustrated in the accompanying Drawings and described in the foregoing Detailed Description, it will be understood that the invention is not limited to the embodiments disclosed, but is capable of numerous rearrangements, modifications, and substitutions of parts and elements without departing from the spirit of the invention.

What is claimed is:

1. A syringe for sequentially administering different fluids comprising:

a syringe body having a hollow interior for receiving the fluids to be administered;

a syringe needle mounted at one end of the syringe body for administering the fluids therefrom;

a plunger mounted within the interior of the syringe body for movement therein toward the end of the syringe body comprising the syringe needle to force fluids outwardly from the interior of the syringe body through the syringe needle;

the plunger further comprising a piston forming a fluid tight seal with the interior of the syringe body;

a floating piston slidably supported within the hollow interior of the syringe body and forming a fluid tight seal with the syringe body which divides the syringe body into a first portion for receiving the first fluid to be administered and a second portion for receiving the second fluid to be administered; and the floating piston further comprising means for connecting the second fluid to be administered in fluid communication with the syringe needle after all of the first fluid to be administered has been discharged therethrough.

2. The syringe according to claim 1 wherein the floating piston is further characterized by an upper portion forming a fluid tight seal with the interior of the syringe body, a lower portion comprising resilient means, and a piercing needle mounted in and supported by the resilient lower portion and having a hollow interior.

3. The syringe according to claim 2 wherein the resilient means of the lower portion comprises a spongy material.

4. The syringe according to claim 2 wherein the resilient means of the lower portion comprises a gas.

5. The syringe according to claim 2 wherein the first portion of the floating piston comprises a non-coring elastomeric material.

6. The syringe according to claim 2 wherein the lower portion of the floating piston comprises a spongy material having the piercing needle mounted therein and a resilient coating surrounding the spongy material.

7. The syringe according to claim 6 wherein the floating piston is further characterized by an upper portion forming a fluid tight seal with the interior of the syringe body, a lower portion comprising resilient means, and a piercing needle mounted in and supported by the resilient lower portion and having a hollow interior.

8. The syringe according to claim 7 wherein the resilient means of the lower portion comprises a spongy material.

9. The syringe according to claim 7 wherein the resilient means of the lower portion comprises a gas.

10. The syringe according to claim 7 wherein the first portion of the floating piston comprises a non-coring elastomeric material.

11. The syringe according to claim 7 wherein the lower portion of the floating piston comprises a spongy material having the piercing needle mounted therein and a resilient coating surrounding the spongy material.

12. The syringe according to claim 1 wherein the syringe needle is characterized by a predetermined diameter, and wherein the piercing needle of the floating piston is characterized by a diameter equal to or greater than the diameter of the syringe needle.

13. For use in conjunction with a syringe of the type comprising a syringe body having a hollow interior, a hollow syringe needle mounted at one end of the syringe body and coupled in fluid communication with the interior thereof, and a plunger mounted for movement within the syringe body toward the syringe needle to force fluids contained within the syringe body outwardly through the syringe needle, the plunger further comprising a piston forming a fluid tight seal with the interior of the syringe body, a floating piston adapting the syringe for the sequential administration of different fluids comprising:

means forming a fluid tight seal with the interior of the syringe body which divides the syringe body into a first portion for receiving a first fluid to be administered and a second portion for receiving a second fluid to be administered; and means for connecting the second portion of the syringe body in fluid communication with the syringe needle after the first fluid to be administered has been discharged from the syringe body through the syringe needle under the action of the plunger.

14. The syringe according to claim 13 wherein the syringe needle is characterized by a predetermined diameter, and wherein the piercing needle of the floating piston is characterized by a diameter equal to or greater than the diameter of the syringe needle.

15. A syringe for sequentially administering different fluids comprising:

a syringe body having a hollow interior for receiving the fluids to be administered;

a syringe needle mounted at one end of the syringe body for administering the fluids therefrom;

a plunger mounted within the interior of the syringe body for movement therein toward the end of the syringe body comprising the syringe needle to force fluids outwardly from the interior of the syringe body through the syringe needle;

the plunger further comprising a piston forming a fluid tight seal with the interior of the syringe body;

a floating piston slidably supported within the hollow interior of the syringe body and forming a fluid tight seal with the syringe body which divides the syringe body into a first portion for receiving the first fluid to be administered and a second portion for receiving the second fluid to be administered; and the floating piston further comprising valve means for initially maintaining separation between the first and second fluids and for connecting the second fluid to be administered in fluid communication with the syringe needle after all of the first fluid to be administered has been discharged therethrough.

16. The syringe according to claim 15 wherein the floating piston comprises a body formed from a resilient material which forms a fluid tight seal with the syringe body.

17. The syringe according to claim 15 wherein the resilient material comprises a spongy material.

18. The syringe according to claim 15 wherein the floating piston has a top surface facing the plunger of the syringe and a bottom surface facing the needle of the syringe, wherein the floating piston has an aperture extending therethrough from the top surface to the bottom surface, and wherein the valve means is mounted in the aperture of the floating piston.

19. The syringe according to claim 18 wherein the valve means comprises an imperforate top plate normally engaging the top surface of the floating piston and extending over the entirety of the aperture formed through the floating piston at the intersection thereof with the top surface.

20. The syringe according to claim 19 wherein the valve means further includes a substantially rigid actuating member secured to the imperforate top plate and extending therefrom through the aperture formed through the floating piston at least to the intersection thereof with the bottom surface of the floating piston, the actuating member being responsive to engagement of the floating piston with the end of the syringe body having the needle mounted therein to disengage the imperforate top plate from the floating piston thereby facilitating fluid flow through the aperture formed through the floating piston.

21. The syringe according to claim 20 wherein the valve means further includes a perforated bottom plate secured to the end of the actuating member remote from the point of attachment thereof to the top plate for normally retaining the imperforate top plate in engagement with the top surface of the floating piston.

22. The syringe according to claim 21 wherein the floating piston comprises a resilient material and wherein the imperforate top plate and the perforated bottom plate comprising the valve means normally retain the resilient material comprising the floating piston in a slightly compressed condition thereby retaining the imperforate top plate in engagement with the top surface of the floating piston.

23. The syringe according to claim 22 wherein further movement of the plunger within the syringe body toward the end of the syringe body comprising the syringe needle following engagement of the floating piston with the end of the syringe body having the needle mounted therein causes compression of the resilient material comprising the floating piston thereby disengaging the imperforate top plate of the valve means from the top surface of the floating piston to facilitate flow of the second fluid through the aperture formed in the floating piston and through the syringe needle.

24. The syringe according to claim 23 wherein the floating piston comprises a resilient, spongy material which maintains a fluid tight seal with the interior of the syringe body.

25. For use in conjunction with a syringe of the type comprising a syringe body having a hollow interior, a hollow syringe needle mounted at one end of the syringe body and coupled in fluid communication with the interior thereof, and a plunger mounted for movement within the syringe body toward the syringe needle to force fluids contained within the syringe body outwardly through the syringe needle, the plunger further comprising a piston forming a fluid tight seal with the interior of the syringe body, a floating piston adapting the syringe for the sequential administration of different fluids comprising:

resilient means forming a fluid tight seal with the interior of the syringe body which divides the syringe body into a first portion for receiving a first fluid to be administered and a second portion for receiving a second fluid to be administered; and valve means for connecting the second portion of the syringe body in fluid communication with the syringe needle after the first fluid to be administered has been discharged from the syringe body through the syringe needle under the action of the plunger.

26. The syringe according to claim 25 wherein further characterized by a floating piston comprising a body formed from a resilient material which forms a fluid tight seal with the syringe body.

27. The syringe according to claim 25 wherein the resilient means comprises a spongy material.

28. The syringe according to claim 25 wherein the resilient means comprises a floating piston having a top surface facing the plunger of the syringe and a bottom surface facing the needle of the syringe, wherein the floating piston has an aperture extending therethrough from the top surface to the bottom surface, and wherein the valve means is mounted in the aperture of the floating piston.

29. The syringe according to claim 28 wherein the valve means comprises an imperforate top plate normally engaging the top surface of the floating piston and extending over the entirety of the aperture formed through the floating piston at the intersection thereof with the top surface.

30. The syringe according to claim 29 wherein the valve means further includes a substantially rigid actuating member secured to the imperforate top plate and extending therefrom through the aperture formed through the floating piston at least to the intersection thereof with the bottom surface of the floating piston, the actuating member being responsive to engagement of the floating piston with the end of the syringe body having the needle mounted therein to disengage the imperforate top plate from the floating piston thereby facilitating fluid flow through the aperture formed through the floating piston.

31. The syringe according to claim 30 wherein the valve means further includes a perforated bottom plate secured to the end of the actuating member remote from the point of attachment thereof to the top plate for normally retaining the imperforate top plate in engagement with the top surface of the floating piston.

32. The syringe according to claim 31 wherein the floating piston comprises a resilient material and wherein the imperforate top plate and the perforated bottom plate comprising the valve means normally retain the resilient material comprising the floating piston in a slightly compressed condition thereby retaining the imperforate top plate in engagement with the top surface of the floating piston.

33. The syringe according to claim 32 wherein further movement of the plunger within the syringe body toward the end of the syringe body comprising the syringe needle following engagement of the floating piston with the end of the syringe body having the needle mounted therein causes compression of the resilient material comprising the floating piston thereby disengaging the imperforate top plate of the valve means from the top surface of the floating piston to facilitate flow of the second fluid through the aperture formed in the floating piston and through the syringe needle.

34. The syringe according to claim 33 wherein the floating piston comprises a resilient, spongy material which maintains a fluid tight seal with the interior of the syringe body.

* * * * *

UNITED STATES PATENT AND TRADEMARK OFFICE
CERTIFICATE OF CORRECTION

| | | |
|---|---|---|
| PATENT NO. | : 7,077,827 B2 | Page 1 of 1 |
| APPLICATION NO. | : 10/788713 | |
| DATED | : July 18, 2006 | |
| INVENTOR(S) | : Christian John Greenfield | |

It is certified that error appears in the above-identified patent and that said Letters Patent is hereby corrected as shown below:

TITLE PAGE, ITEM (75)

For the address of Inventor, Christian Greenfield, replace "827 Morado Pl., Oxnard, CA 93030" with --1014 Via Regina, Santa Barbara, CA 93111--.

Col. 1, line 66, replace "floating compartment 5" with --floating plunger 5--.

Col. 4, line 57, replace "out in,the barrel" with -- out in the barrel--.

Signed and Sealed this

Seventh Day of November, 2006

JON W. DUDAS
*Director of the United States Patent and Trademark Office*